United States Patent
Shalaby et al.

(10) Patent No.: US 8,507,614 B2
(45) Date of Patent: Aug. 13, 2013

(54) MULTIPHASIC ABSORBABLE COMPOSITIONS OF SEGMENTED L-LACTIDE COPOLYMERS

(75) Inventors: Shalaby W Shalaby, Anderson, SC (US); Michael Scott Taylor, Pendleton, SC (US); Shawn J. Peniston, Easley, SC (US)

(73) Assignee: Poly-Med, Inc., Anderson, SC (US)

( * ) Notice: Subject to any disclaimer, the term of this patent is extended or adjusted under 35 U.S.C. 154(b) by 1052 days.

(21) Appl. No.: 12/322,841

(22) Filed: Feb. 7, 2009

(65) Prior Publication Data
US 2009/0204116 A1    Aug. 13, 2009

Related U.S. Application Data

(60) Provisional application No. 61/063,898, filed on Feb. 7, 2008.

(51) Int. Cl.
*C08G 63/91* (2006.01)

(52) U.S. Cl.
USPC ........... 525/411; 525/410; 525/415; 525/450; 606/151; 606/219; 606/908; 606/910

(58) Field of Classification Search
USPC ................. 525/410, 411, 415, 450; 606/151, 606/219, 908, 910
See application file for complete search history.

(56) References Cited

U.S. PATENT DOCUMENTS

| | | | |
|---|---|---|---|
| 4,741,337 A | 5/1988 | Smith et al. | |
| 4,889,119 A | 12/1989 | Jamiolkowski et al. | |
| 5,525,646 A * | 6/1996 | Lundgren et al. | 523/105 |
| 2006/0193892 A1 * | 8/2006 | Furst et al. | 424/426 |
| 2008/0033540 A1 * | 2/2008 | Wang et al. | 623/1.49 |

OTHER PUBLICATIONS

Dobrzynski, P., et al; Biomacromolecules, 2005, vol. 6, p. 483-488.*
Lee, S.H., et al; Journal of Biomedical Materials Research Part A, 2003, p. 29-37.*
Callari, J.J.; Plastics World, Nov. 1994, p. 20-22.*

* cited by examiner

*Primary Examiner* — Robert Jones, Jr.
(74) *Attorney, Agent, or Firm* — McCormick, Paulding & Huber LLP

(57) ABSTRACT

Absorbable, multiphasic, crystalline, solid blend compositions having at least two first order thermal transitions, are formed of a segmented l-lactide copolymer as the principal or major component and at least one additional crystalline thermoplastic absorbable polyester having glycolide-based sequences, a fraction of which participated in ester-ester interchange reactions with lactide-based sequences to produce crystalline materials with modulated properties for use in producing orthopedic and tissue-repair devices.

16 Claims, No Drawings

MULTIPHASIC ABSORBABLE COMPOSITIONS OF SEGMENTED L-LACTIDE COPOLYMERS

The present application claims the benefit of prior provisional application U.S. Ser. No. 61/063,898, filed Feb. 7, 2008.

FIELD OF THE INVENTION

This invention relates to multiphasic, solid, absorbable compositions of a segmented l-lactide copolymer as the principal or major component and at least one additional thermoplastic absorbable polymer capable of ester-ester interchange with the chains of the molten principal component to produce a multiphasic, absorbable material with modulated molecular intermixing between the constituent components to form medical devices or parts thereof having tailored absorption and mechanical strength retention profile under physiologic conditions.

BACKGROUND OF THE INVENTION

Polymer melt-blending has been used for decades in the area of non-absorbable industrial thermoplastic, heterochain, and homochain polymers to produce different polymer blends (or polyblends) exhibiting a range of physicomechanical properties to meet specific requirements of a broad spectrum of industrial and medical products. However, because of the chemical nature of the non-absorbable components of these polyblends, practically no chemical interaction takes place upon melt-blending of the components and there has been virtually no interest in achieving such interactions. And with the development of biomedical absorbable polyesters having reactive chains, more attention was directed to the maintenance of the integrity of these chains during the melt processing of crystalline block and segmented copolyesters, where uncontrolled ester-ester interchange can lead to a decrease or total loss of crystallinity. Subsequently, the lack of understanding and ability to control the ester-ester interchange reaction in molten absorbable polyesters has discouraged investigators of the prior art to exploit melt-blending of different polyesters as a means to form absorbable polyblends with unique properties, as has been the practice with non-absorbable polyblends. Interestingly, one of the present inventors and his earlier coworkers ventured to use melt-blending to yield two-component composites under conditions that did not alter the initial physicochemical properties of these components, which independently co-existed in the solid state (U.S. Pat. Nos. 4,741,337 and 4,889,119). More specifically, the latter prior art dealt with surgical, fasteners comprising a glycolide-rich blend of two or more polymers, one polymer being a high-lactide content polymer and another being a high-glycolide content polymer. The blend as a whole contains from 65 to 84 weight percent polymerized glycolide with the high-glycolide content polymer constituting at least 50 weight percent of the blend. Regrettably, development of these blends failed to lead to a marketable product of the sought medical devices. This failure was attributed to the high content of the fast-absorbing glycolide-based major component of the blends and uncontrolled physicochemical events that might have prevailed during melt-blending, resulting in non-predictable changes in the device properties when used in the intended biological environment. Such unfruitful use of melt-blending provided the incentive to pursue the study subject of the instant invention that deals with the use of slow-absorbing, high lactide-based segmented copolymers as the principal component in specially selected compositions that permit controlling the extent of the ester-ester interchange reaction and hence, the molecular intermixing to produce multiphasic crystalline solid materials with predictable properties for use in new or existing forms of medical devices.

SUMMARY OF THE INVENTION

Accordingly, the present invention is directed to an absorbable, multiphasic, crystalline, solid blend composition which is at least 45 percent by weight of a major component of a segmented l-lactide copolymer, at least one minor component which at least one additional crystalline thermoplastic absorbable polyester having glycolide-based sequences, a fraction of the glycolide sequences interchanged with a fraction of the lactide sequences of the major component, the overall composition exhibiting at least two first order thermal transitions with a peak temperature difference exceeding 10° C., the overall composition having a crystallinity of at least 10 percent of the crystallinity of the major component as measured in terms of heat of fusion ($\Delta H_f$), wherein the crystallinity decreases as the number of interchanged glycolide and lactide sequences increases.

Preferably, the major component is a segmented copolymer of from about 80 to about 95 molar percent of l-lactide and from about 20 to about 5 molar percent of trimethylene carbonate and the minor component is a glycolide copolymer. It is also preferred that the glycolide copolymer is a copolymer of from about 90 to about 99 molar percent glycolide and from about 10 to about 1 molar percent l-lactide. As such preferably the major component exhibits an inherent viscosity of at least about 1.8 dL/g (in chloroform) and the minor component exhibits an inherent viscosity of at least about 1.0 dL/g (in hexafluoroisopropyl alcohol). And preferably the major component is present in from about 75 to about 90 weight percent of the overall composition and the glycolide copolymer is present in from about 25 to about 10 weight percent of the overall composition.

In another preferred embodiment the major component is a segmented copolymer of from about 80 to about 95 molar percent of l-lactide and from about 20 to about 5 molar percent of trimethylene carbonate and the minor component comprises an ϵ-caprolactone copolymer and a glycolide-rich polymer. For such embodiment the major component exhibits an inherent viscosity of at least about 1.8 dL/g (in chloroform) and the minor component exhibits an inherent viscosity of at least about 0.9 dL/g, and, preferably the glycolide-rich polymer has more than 60 glycolide-based sequences. In a preferred embodiment the ϵ-caprolactone copolymer is a copolymer of from about 90 to about 99 molar percent of ϵ-caprolactone and from about 10 to about 1 molar percent of glycolide and the glycolide-rich polymer is an acid terminated polyglycolide. Most preferably the acid-terminated polyglycolide comprises solid microparticles exhibiting a heat of fusion of at least 60 J/g.

Thus, in a preferred embodiment the present invention is directed to a totally absorbable multiphasic, crystalline, solid composition exhibiting at least two first order thermal transitions with peak temperature difference exceeding 10° C. comprising at least about 45 weight percent of a segmented l-lactide copolymer as the principal or a major component, and at least one additional crystalline thermoplastic absorbable polyester component comprising glycolide-based sequences that participated in ester-ester interchange reactions with the lactide-based sequences of the principal or a major component in the molten state at temperatures not exceeding about 35° C. above the melting temperature of the highest melting major component of the said composition, while retaining at least 10 percent of initial crystallinity of the individual principal or major components as measured in terms of heat of fusion ($\Delta H_f$), wherein the principal or a major component is a segmented copolymer of about 88/12 (molar) l-lactide/trimethylene carbonate and the said at least one additional thermoplastic polyester component comprising a glycolide copolymer, and wherein the glycolide copolymer comprising a copolymer made from about 95/5 (molar) glycolide/l-lactide. Meanwhile, the principal or a major component and the 95/5 glycolide/l-lactide copolymer exhibit an inherent viscosity of at least about 1.8 dL/g (in chloroform) and 1.0 dL/g (in hexafluoro-isopropyl alcohol), respectively, and represent 85 and 15 weight percent, respectively, of the total composition.

Another aspect of this invention deals with a totally absorbable multiphasic, crystalline, solid composition exhibiting at least two first order thermal transitions with peak temperature difference exceeding 10° C. comprising at least about 45 weight percent of a segmented l-lactide copolymer as the principal or a major component, and at least one additional crystalline thermoplastic absorbable polyester component comprising glycolide-based sequences that participated in ester-ester interchange reactions with the lactide-based sequences of the principal or a major component in the molten state at temperatures not exceeding about 35° C. above the melting temperature of the highest melting major component of the said composition, while retaining at least 10 percent of initial crystallinity of the individual principal or major components as measured in terms of heat of fusion ($\Delta H_f$), wherein the said major component is a segmented copolymer of about 88/12 (molar) l-lactide/trimethylene carbonate and the said at least one additional thermoplastic polyester component comprises an ε-caprolactone copolymer and a glycolide-rich polymer, and wherein the l-lactide/trimethylene carbonate copolymer and ε-caprolactone copolymer exhibit an inherent viscosity in chloroform of at least about 1.8 and 0.9 dL/g, respectively, and the chains of the glycolide-rich polymer comprise more than 60 glycolide-based sequences. Meanwhile, the ε-caprolactone copolymer is made from 90-99/10-1 (molar) ε-caprolactone/glycolide and the glycolide-rich polymer is an acid terminated polyglycolide which comprises solid microparticles exhibiting a heat of fusion of at least 60 J/g. Furthermore, the multiphasic composition is processed into an absorbable outer component of a thermo-mechanically deformable, reversibly inflatable metallic scaffold for use as intramedullary bone fixation devices such as a bone pin or rod and a reversibly inflatable bone stent for internal repair of human or animal cancellous bones.

From a biomedical application perspective, this invention deals with a totally absorbable multiphasic, crystalline, solid composition exhibiting at least two first order thermal transitions with peak temperature difference exceeding 10° C. comprising at least about 45 weight percent of a segmented l-lactide copolymer as the principal or a major component, and at least one additional crystalline thermoplastic absorbable polyester component comprising glycolide-based sequences that participated in ester-ester interchange reactions with the lactide-based sequences of the principal or a major component in the molten state at temperatures not exceeding about 35° C. above the melting temperature of the highest melting major component of the said composition, while retaining at least 10 percent of initial crystallinity of the individual principal or major components as measured in terms of heat of fusion ($\Delta H_f$), wherein the said multiphasic composition is in the form of a wound repair device or an absorbable component of a surgical device for use in anchoring a second device to repair or replace living tissue in humans and animals, and wherein the wound repair device is a staple for tissue repair or fastener for anchoring a surgical mesh to repair living tissues. More specifically, the fastener and surgical mesh are used for hernial repair.

A specific aspect of this invention addresses a totally absorbable multiphasic, crystalline, solid composition exhibiting at least two first order thermal transitions with peak temperature difference exceeding 10° C. comprising at least about 45 weight percent of a segmented l-lactide copolymer as the principal or a major component, and at least one additional crystalline thermoplastic absorbable polyester component comprising glycolide-based sequences that participated in ester-ester interchange reactions with the lactide-based sequences of the principal or a major component in the molten state at temperatures not exceeding about 35° C. above the melting temperature of the highest melting major component of the said composition, while retaining at least 10 percent of initial crystallinity of the individual principal or major components as measured in terms of heat of fusion ($\Delta H_f$), wherein the said major component is a segmented copolymer of about 88/12 (molar) l-lactide/trimethylene carbonate and the said at least one additional thermoplastic polyester component comprises an ε-caprolactone copolymer and a glycolide-rich polymer, and wherein the l-lactide/trimethylene carbonate copolymer and ε-caprolactone copolymer exhibit an inherent viscosity in chloroform of at least about 1.8 and 0.9 dL/g, respectively, and the chains of the glycolide-rich polymer comprise more than 60 glycolide-based sequences while the said multiphasic composition is processed into a fastener or staple for use in repairing living tissues.

Another specific aspect of the present invention deals with a totally absorbable multiphasic, crystalline, solid composition exhibiting at least two first order thermal transitions with peak temperature difference exceeding 10° C. comprising at least about 45 weight percent of a segmented l-lactide copolymer as the principal or a major component, and at least one additional crystalline thermoplastic absorbable polyester component comprising glycolide-based sequences that participated in ester-ester interchange reactions with the lactide-based sequences of the principal or a major component in the molten state at temperatures not exceeding about 35° C. above the melting temperature of the highest melting major component of the said composition, while retaining at least 10 percent of initial crystallinity of the individual principal or major components as measured in terms of heat of fusion ($\Delta H_f$), wherein the said multiphasic composition is in the form of an orthopedic device or part of an orthopedic device for use in repairing or correcting bone defects and wherein the orthopedic device is a bone pin, intramedullary rod, and the said multiphasic composition is a component of a metal-supported composite bone stent or intramedullary rod.

DETAILED DESCRIPTION OF PREFERRED EMBODIMENTS

This invention relates to a totally absorbable, multiphasic, crystalline solid, absorbable blend composition of a segmented l-lactide copolymer as the principal or a major component representing at least about 45 to 55 weight percent for injection molded compositions and at least about 55 to 95 weight percent of melt-extruded compositions. In addition to the segmented l-lactide copolymer, the multiphasic compositions comprise at least one thermoplastic, absorbable polymer capable of ester-ester interchange with the chain of the molten, segmented l-lactide copolymer during melt-processing by extrusion and or injection molding to produce multiphasic, absorbable materials with modulated molecular intermixing between the constituent components. In effect, a typical resultant material of the melt-processing comprises (1) a fraction of unaltered chains of the initial components; and (2) hybrid chains formed by the ester-ester interchange of a fraction of the l-lactide copolymeric chain and at least one of the chains of other polymeric components of the initial unprocessed blend. The hybrid chains, comprising at least two types of chain sequences, serve as a polymeric surfactant capable of dispersing the different mutually immiscible phases comprising the unaltered chains. The fraction of the hybrid chains relative to the practically unaltered chains in the compositions subject of the instant invention was controlled by using a moderately reactive copolymeric l-lactide chains as the principal or a major component in combination with (1) highly reactive, high melting polymers comprising copolymeric glycolide chains to yield crystalline, high modulus, biphasic or triphasic compositions exhibiting at least a bimodal thermal transition, or (2) low melting polymers comprising slow-reacting copolymeric ε-caprolactone chains to yield crystalline compositions displaying at least a bimodal thermal transition and thermomechanical properties. Contrary to the teaching of the prior art where melt-blending caused virtually no change or complete loss in the crystallinity and related properties of the constituent polymers, the present invention relies on (1) using an unprecedented selection of the constituent polymeric components to yield multiphasic compositions exhibiting modulated thermal and physicomechanical properties; and (2) applying carefully controlled melt-processing conditions, as in melt temperature, to control the extent of the ester-ester interchange reaction and hence, achieve the sought degree of hybrid chain formation, phase mixing, dispersion of immiscible phases, and extent of molecular chain intermixing—this entails mixing of different, unaltered chains as well as hybrid chains.

Specific processing conditions and properties of resulting multiphasic solid, crystalline compositions are summarized in Tables I through IV of Examples 1 through 5. Controlled changes in the thermal properties of typical extruded and injection molded compositions are summarized in Tables II through IV. The changes in the melting temperature and heat of fusion grossly reflect the extent of the controlled ester-ester interchange reaction, a novel feature of the instant invention. The basic changes in the thermal transitions are paralleled by changes in the physicomechanical properties of multiphasic compositions processed into extruded or injection molded test specimens. Examples of the changes sought of the successful application of a monofilament composition and three injection molded compositions are illustrated by the data in Tables I through IV. From a medical application perspective, this invention deals, in part, with monofilament and injection molded multiphasic articles for use as components of an absorbable fastener to repair living tissues or to anchor an absorbable or non-absorbable device intended for repairing defective living tissues as in meshes for hernial repair. Another aspect of the instant invention deals with multiphasic injection molded devices or insert-molded components of metallic devices intended for use in orthopedic applications as in internal bone repairs. For instance, metallic/absorbable polymer-containing devices made by insert molding a multiphasic absorbable composition selected from those noted in Tables II through IV can be used as an intramedullary fixation device (or stent) having unique thermomechanical properties that facilitate their placement and retrieval by orthopedic surgeons. More specifically, an application of multiphasic composition analogous to the bicomponent system in Table I is their use as a device or components thereof for use in tissue repair or anchoring a hernial mesh, wherein said multiphasic absorbable system exhibits a faster rate of degradation, higher degree of stiffness (or modulus), higher strength and lower percent elongation compared with the principal or major component, SMC-7. Another specific application of multiphasic compositions analogous to the triphasic system in Tables II through IV is their use as a component of insert molded, partially metallic orthopedic devices as in the case of intramedular rods or stent, wherein such application calls for the said multiphasic, absorbable composition to exhibit bimodular flexural modulus, slow absorption and strength loss profiles, faster rate of crystallization by virtue of an absorbable nucleating agent representing one component of the triphasic systems, and reversible thermo-mechanical transition as compared to the principal or major polymeric component, i.e., SMC-7. Further illustrations of the present invention are provided by the following examples:

EXAMPLE 1

Preparation of Typical Extruded Biphasic Monofilament Fibers

To prepare the blended polymeric precursor for extrusion into biphasic monofilaments, individual components were added to a glass jar and placed on a rolling apparatus for at least 2 hours. When mixing was complete, the polymer mixture was fed through a ¾"-diameter single screw extruder with a metering pump to assure constant extrusion rate. The polymer was heated incrementally in the extruder from an initial temperature zone of 180° C. to 240° C. at the nozzle. The blended extrudate was cooled in a water bath and collected on spools with a diameter of 1.95 mm. Fiber strength was improved by orientation in two stages at 70° C. and 95° C., respectively, with a total 5× draw ratio. The fiber morphology was stabilized by annealing at 80° C. for 1 hour.

Tensile properties of oriented and annealed specimen were obtained using an MTS Synergie 200 test frame equipped with TestWorks software and fiber cam-action grips with a gage length of 70 mm. Inherent viscosity was measured using a Canon-Fenske viscometer and thermal properties were determined using a Perkin-Elmer DSC 6.

TABLE I

Components of a Typical Biphasic Composition (BP) Based on 85 Weight Percent SMC-7 and Properties of Extruded Monofilaments Thereof

| Tested Property | | Starting Polymer Components | | Annealed Single-Component Extruded Monofilaments | | Annealed Biphasic Extruded Monofilaments |
| --- | --- | --- | --- | --- | --- | --- |
| | | SMC-7 | MX-2 | SMC-7 | MX-2 | |
| Weight Percent of Components | | 100 | 100 | 100 | 100 | 85 SMC-7/ 15 MX-2 |
| Inherent Viscosity | In HFIP[a] | 2.66 | 1.5 | — | — | 1.55 |
| | In CHCl$_3$ | 2.59 | — | 1.90 | — | — |
| Thermal Properties of Annealed Specimen | $T_m$, ° C. | 185 | 209 | 163 | 211 | SMC-7, 163 & MX-2, 210 |
| | $\Delta H_f$, J/g | 60 | 63 | 40 | 65 | SMC-7, 40 & MX-2, 8.0 |

TABLE I-continued

Components of a Typical Biphasic Composition (BP) Based on 85 Weight Percent SMC-7 and Properties of Extruded Monofilaments Thereof

| Tested Property | Starting Polymer Components | | Annealed Single-Component Extruded Monofilaments | | Annealed Biphasic Extruded Monofilaments |
|---|---|---|---|---|---|
| | SMC-7 | MX-2 | SMC-7 | MX-2 | |
| Maximum Processing Temperature, °C. | — | — | 238 | 245 | 240 |

Key Physical Properties of Extruded and Annealed Monofilaments

| | | | | | |
|---|---|---|---|---|---|
| Diameter, mm | — | — | 1.04 | 0.036 | 1.07 |
| Tensile Strength, kpsi | — | — | 31 | 183 | 34 |
| Tensile Modulus, kpsi | — | — | 330 | 1000 | 350 |
| Ultimate Strain, % | — | — | 91 | 18 | 81 |
| Flexural Load at Yield, N | — | — | 3.44 | — | 4.10 |
| Flexural Modulus, MPa | — | — | 1020 | — | 840 |

[a]HFIP = Hexafluoroisopropyl alcohol.

EXAMPLE 2

Preparation of Injection Molded Typical Triphasic Compositions: A General Method The preparation of triphasic composition was exemplified using tensile specimens comprising a high melting l-lactide segmented copolyester (SMC-7), a low melting, virtually random ε-caprolactone-glycolide copolymer (PCLM12), and high melting, highly crystalline microparticular polyglycolide (A6), as a nucleating agent. This was accomplished by first physical mixing of the constituents in the desired ratios using common glass jars and a rolling apparatus to provide prolonged and continuous mixing. Upon complete mixing of the components the mixture was fed into a ½" diameter single screw extruder using a metering feeder such that the feed rate was matched to the generation of extrudate. The extruder was set to a nominal rotational speed with a profiled temperature starting at 90° C. in the feed throat and reaching 182° C. at the nozzle. Blended extrudate was collected on a stainless steel conveyor which was monitored to achieve extrudate diameters between 2 mm and 3 mm. Following cooling on the conveyor, the extrudate was spooled for ease of subsequent processing. Spooled extrudate was fed into a pelletizer where it was cut to lengths between 3 mm and 6 mm.

Pelletized extrudate was then injection molded using an Arburg 30 ton injection molding machine utilizing an injection mold featuring the geometry of a tensile specimen with thickness of 1.5 mm and profile as detailed in ASTM D638 for Type V specimens. Injection molding melt temperatures did not exceed 192° C. and injection flow rates between 4 and 5 cubic centimeters per second were used resulting in a maximum injection pressure of approximately 1500 bar. Mold temperatures ranged between 19° C. and 25° C. depending on the ratio of the triphasic components with mixtures containing increased levels of PCLM molded at the lower values of the range. Molded specimens were annealed at 80° C. for 1 hour in an unconstrained state to maximize the level of crystallinity for the SMC-7 component.

EXAMPLES 3-5

Evaluation of Injection Molded Tensile Specimens of Three Typical Triphasic Compositions Tables II through IV summarize the molding conditions of test specimens made as per the general method of Example 2 and physicomechanical properties.

TABLE II

A Typical Triphasic Composition (TP-I) Based on 54 Percent SMC-7 and Properties of Injection Molded Tensile Specimens

| | Tested Property | Starting Polymer Components | | | Annealed Single Component as Type V Tensile Specimen | | Annealed Triphasic Injection Molded Type V Tensile Specimens (SMC-7/ PCLM12/A6) |
|---|---|---|---|---|---|---|---|
| | | SCM-7 | PCLM12 | A6 | SCM-7 | PCLM12 | |
| | Weight Percent of Components | 100 | 100 | 100 | 100 | 100 | 54/44/2 |
| | Inherent Viscosity, dL/g in Chloroform | 2.53 | 1.72 | — | 1.90 | 1.61 | — |
| Thermal Properties of Annealed Specimens | $T_m$, °C. (DSC)[a] | 183.5 | 62.5 | 217.1 | 171.7 | 59.5 | 168.9/61.1/ 219.1 |
| | $\Delta H_f$, J/g (DSC)[b] | 64.4 | 68.5 | 110.0 | 29.6 | 41.5 | 16.6/37.2/1.6 |
| | $T_g$, °C. (DMA)[c] | — | — | — | — | — | 73.8 |
| Maximum Processing Temperature[d] | Step One, °C. | — | — | — | — | — | 182 |
| | Step Two, °C. | — | — | — | 200 | 120 | 192 |
| Key Physical | Thickness, mm | — | — | — | 1.5 | 1.5 | 1.5 |

TABLE II-continued

A Typical Triphasic Composition (TP-I) Based on 54 Percent SMC-7 and
Properties of Injection Molded Tensile Specimens

| Tested Property | | Starting Polymer Components | | | Annealed Single Component as Type V Tensile Specimen | | Annealed Triphasic Injection Molded Type V Tensile Specimens (SMC-7/ PCLM12/A6) |
|---|---|---|---|---|---|---|---|
| | | SCM-7 | PCLM12 | A6 | SCM-7 | PCLM12 | |
| Properties | Modulus, MPa | — | — | — | 2186.8 | 313.0 | 1313.3 |
| | Peak Stress, MPa | — | — | — | 115.82 | 27.58 | 40.67 |
| | Elongation at Break, % | — | — | — | 4.5 | 417.0 | 11.0 |

[a]Individual component melt temperatures for PCLM12, SMC-7, and A6, respectively.
[b]Individual component heat of fusion values for PCLM12, SMC-7, and A6, respectively.
[c]Glass transition temperature for the SMC-7 component determined by dynamic mechanical analysis using tan delta.
[d]Processing in step one and step two entail melt-blending in a single screw extruded and injection molding into tensile specimens, respectively.

TABLE III

A Typical Triphasic Composition (TP-II) Based on 49 Percent SMC-7 and
Properties of Injection Molded Tensile Specimens

| Tested Property | | Starting Polymer Components | | | Annealed Single Component as Type V Tensile Specimen | | Annealed Triphasic Injection Molded Type V Tensile Specimens (SMC-7/PCLM12/A6) |
|---|---|---|---|---|---|---|---|
| | | SCM-7 | PCLM12 | A6 | SCM-7 | PCLM12 | |
| Weight Percent of Components | | 100 | 100 | 100 | 100 | 100 | 49/49/2 |
| Inherent Viscosity, dL/g in Chloroform | | 2.53 | 1.72 | — | 1.90 | 1.61 | — |
| Thermal Properties of Annealed Specimens | $T_m$, °C. (DSC)[a] | 183.5 | 62.5 | 217.1 | 171.7 | 59.5 | 166.7/56.1/220.0 |
| | $\Delta H_f$, J/g (DSC)[b] | 64.4 | 68.5 | 110.0 | 29.6 | 41.5 | 14.2/29.1/1.6 |
| | $T_g$, °C. (DMA)[c] | — | — | — | — | — | 75.4 |
| Maximum Processing Temperature[d] | Step One, °C. | — | — | — | — | — | 182 |
| | Step Two, °C. | — | — | — | 200 | 120 | 192 |
| Key Physical Properties | Thickness, mm | — | — | — | 1.5 | 1.5 | 1.5 |
| | Modulus, MPa | — | — | — | 2186.8 | 313.0 | 1215.4 |
| | Peak Stress, MPa | — | — | — | 115.82 | 27.58 | 37.23 |
| | Elongation at Break, % | — | — | — | 4.5 | 417.0 | 15.0 |

[a]Individual component melt temperatures for PCLM12, SMC-7, and A6, respectively.
[b]Individual component heat of fusion values for PCLM12, SMC-7, and A6, respectively.
[c]Glass transition temperature for the SMC-7 component determined by dynamic mechanical analysis using tan delta.
[d]Processing in step one and step two entail melt-blending in a single screw extruded and injection molding into tensile specimens, respectively.

TABLE IV

A Typical Triphasic Composition (TP-III) Based on 39 Percent SMC-7 and
Properties of Injection Molded Tensile Specimens

| Tested Property | | Starting Polymer Components | | | Annealed Single Component as Type V Tensile Specimen | | Annealed Triphasic Injection Molded Type V Tensile Specimens (SMC-7/PCLM12/A6) |
|---|---|---|---|---|---|---|---|
| | | SCM-7 | PCLM12 | A6 | SCM-7 | PCLM12 | |
| Weight Percent of Components | | 100 | 100 | 100 | 100 | 100 | 39/59/2 |
| Inherent Viscosity, dL/g in Chloroform | | 2.53 | 1.72 | — | 1.90 | 1.61 | — |
| Thermal Properties of Annealed | $T_m$, °C. (DSC)[a] | 183.5 | 62.5 | 217.1 | 171.7 | 59.5 | 166.7/60.8/219.6 |
| | $\Delta H_f$, J/g (DSC)[b] | 64.4 | 68.5 | 110.0 | 29.6 | 41.5 | 12.7/41.3/1.6 |

TABLE IV-continued

A Typical Triphasic Composition (TP-III) Based on 39 Percent SMC-7 and Properties of Injection Molded Tensile Specimens

| Tested Property | | Starting Polymer Components | | | Annealed Single Component as Type V Tensile Specimen | | Annealed Triphasic Injection Molded Type V Tensile Specimens (SMC-7/ PCLM12/A6) |
|---|---|---|---|---|---|---|---|
| | | SCM-7 | PCLM12 | A6 | SCM-7 | PCLM12 | |
| Specimens | $T_g$, °C. (DMA)[c] | — | — | | — | — | 74.2 |
| Maximum Processing Temperature[d] | Step One, °C. | — | — | | — | — | 182 |
| | Step Two, °C. | | — | | 200 | 120 | 192 |
| Key Physical Properties | Thickness, mm | — | — | — | 1.5 | 1.5 | 1.5 |
| | Modulus, MPa | — | — | — | 2186.8 | 313.0 | 1187.1 |
| | Peak Stress, MPa | — | — | — | 115.82 | 27.58 | 34.45 |
| | Elongation at Break, % | — | — | — | 4.5 | 417.0 | 15.8 |

[a]Individual component melt temperatures for PCLM12, SMC-7, and A6, respectively.
[b]Individual component heat of fusion values for PCLM12, SMC-7, and A6, respectively.
[c]Glass transition temperature for the SMC-7 component determined by dynamic mechanical analysis using tan delta.
[d]Processing in step one and step two entail melt-blending in a single screw extruded and injection molding into tensile specimens, respectively.

The tensile properties of molded and annealed specimens were obtained using a MTS MiniBionix Universal Tester (model 858) equipped with knurled grips set to a gage length of 25.4 mm. All reported data is an average of four measurements with standard deviations indicated.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. An absorbable, multiphasic, crystalline, solid blend composition comprising at least 45 percent by weight of a major component comprising a segmented l-lactide copolymer, at least one minor component comprising at least one additional crystalline thermoplastic absorbable polyester having glycolide-based sequences, a fraction of the glycolide sequences interchanged with a fraction of the lactide sequences of the major component, the overall composition exhibiting at least two first order thermal transitions with a peak temperature difference exceeding 10° C., the overall composition having a crystallinity of at least 10 percent of the crystallinity of the major component as measured in terms of heat of fusion ($\Delta H_f$), wherein the crystallinity decreases as the number of interchanged glycolide and lactide sequences increases; and
wherein the composition is formed through a melt blending process that includes a controlled ester-ester interchange reaction.

2. An absorbable multiphasic, crystalline, solid blend composition as in claim 1 wherein the major component comprises a segmented copolymer of from about 80 to about 95 molar percent of l-lactide and from about 20 to about 5 molar percent of trimethylene carbonate and the minor component comprises a glycolide copolymer.

3. An absorbable multiphasic, crystalline, solid blend composition as in claim 2 wherein the glycolide copolymer comprises a copolymer of from about 90 to about 99 molar percent glycolide and from about 10 to about 1 molar percent l-lactide.

4. An absorbable, multiphasic, crystalline solid blend composition as in claim 3 wherein the major component exhibits an inherent viscosity of at least about 1.8 dL/g (in chloroform) and the minor component exhibits an inherent viscosity of at least about 1.0 dL/g (in hexafluoroisopropyl alcohol).

5. An absorbable multiphasic, crystalline, solid blend composition as in claim 3 wherein the major component is present in from about 75 to about 90 weight percent of the overall composition and the glycolide copolymer is present in from about 25 to about 10 weight percent of the overall composition.

6. An absorbable multiphasic, crystalline solid blend composition as in claim 1 wherein the major component comprises a segmented copolymer of from about 80 to about 95 molar percent of l-lactide and from about 20 to about 5 molar percent of trimethylene carbonate and the minor component comprises an e-caprolactone copolymer and a glycolide-rich polymer.

7. An absorbable multiphasic, crystalline solid blend composition as in claim 6 wherein the wherein the major component exhibits an inherent viscosity of at least about 1.8 dL/g (in chloroform) and the minor component exhibits an inherent viscosity of at least about 0.9 dL/g, and where the chains of the glycolide-rich polymer comprise more than 60 glycolide-based sequences.

8. An absorbable multiphasic, crystalline solid blend composition as in claim 7 wherein the e-caprolactone copolymer is a copolymer of from about 90 to about 99 molar percent of e-caprolactone and from about 10 to about 1 molar percent of glycolide and wherein the glycolide-rich polymer is an acid terminated polyglycolide.

9. An absorbable multiphasic, crystalline solid blend composition as in claim 8 wherein the acid-terminated polyglycolide comprises solid microparticles exhibiting a heat of fusion of at least 60 J/g.

10. An absorbable multiphasic, crystalline solid blend composition as in claim 1 in the form of a wound repair device or an absorbable component of a surgical device for use in anchoring a second device to repair or replace living tissue in humans and animals.

11. An absorbable multiphasic, crystalline solid blend composition as in claim 10 wherein the wound repair device is a staple for tissue repair or a fastener for anchoring a surgical mesh to repair living tissues.

12. An absorbable multiphasic, crystalline solid blend composition as in claim 11 wherein the surgical mesh is used for hernial repair.

13. An absorbable multiphasic, crystalline solid blend, composition as in claim 7 in the form of a fastener or staple for use in repairing living tissues.

14. An absorbable multiphasic, crystalline solid blend composition as in claim 1 in the form of an orthopedic device or part of an orthopedic device for use in repairing or correcting bone defects.

15. An absorbable multiphasic, crystalline solid blend composition as in claim 14 wherein the orthopedic device is a bone pin, intramedullary rod, and the composition is a component of a metal-supported composite bone stent or intramedullary rod.

16. An absorbable multiphasic, crystalline solid blend composition as in claim 9 in the form of an absorbable outer component of a thermo-mechanically deformable, reversibly inflatable metallic scaffold for use as an intramedullary bone fixation device selected from a bone pin and a rod, and a reversibly inflatable bone stent for internal repair of human or animal cancellous bones.

* * * * *